US007194907B2

(12) United States Patent
Abbate et al.

(10) Patent No.: US 7,194,907 B2
(45) Date of Patent: Mar. 27, 2007

(54) METHOD FOR MEASURING PART THICKNESS HAVING AN EXTERNAL COATING USING IMPEDANCE MATCHING DELAY LINES

(75) Inventors: Agostino Abbate, Boxborough, MA (US); Paul Joseph DeAngelo, West Bridgewater, MA (US); Steven Abe LaBreck, Boston, MA (US)

(73) Assignee: R/D Tech Instruments Inc., Quebec (CA)

( * ) Notice: Subject to any disclaimer, the term of this patent is extended or adjusted under 35 U.S.C. 154(b) by 89 days.

(21) Appl. No.: 10/461,382

(22) Filed: Jun. 16, 2003

(65) Prior Publication Data

US 2004/0250624 A1 Dec. 16, 2004

(51) Int. Cl.
*G01N 29/07* (2006.01)

(52) U.S. Cl. ............................ 73/597; 73/598; 73/602

(58) Field of Classification Search ................. 73/597, 73/602, 579, 590, 600, 599, 53.04, 53.06, 73/54.25, 630, 632, 861.23, 861.27, 598, 73/1.03

See application file for complete search history.

(56) References Cited

U.S. PATENT DOCUMENTS 3,174,120 A * 3/1965 Brouneus .................... 333/143
3,663,842 A * 5/1972 Miller ........................ 310/338
3,688,222 A * 8/1972 Lieberman .................. 333/149
4,207,772 A * 6/1980 Stoller ......................... 73/620
4,275,597 A * 6/1981 Quedens et al. .............. 73/618
4,523,122 A * 6/1985 Tone et al. ................. 310/334
5,201,225 A 4/1993 Takahashi et al. ............ 73/615
5,708,209 A * 1/1998 Stiffler et al. ................. 73/644
5,983,730 A * 11/1999 Freund et al. ........... 73/861.28
6,089,094 A * 7/2000 Zeng et al. .................... 73/579
6,122,968 A * 9/2000 Vandervalk .................. 73/642
6,282,962 B1 * 9/2001 Koch et al. .................... 73/602
6,330,831 B1 * 12/2001 Lynnworth et al. ...... 73/861.28
6,626,049 B1 9/2003 Ao et al. ................. 73/861.29
2002/0134159 A1 9/2002 He ............................. 73/579
2003/0172743 A1 9/2003 Ao et al. ................. 73/861.29

FOREIGN PATENT DOCUMENTS

EP 0878691 11/1998
JP 02205771 8/1990
SU 868351 9/1981

OTHER PUBLICATIONS

Panametrics Technical Notes, pp. 32-40 (2002).
Panametrics XMT868 Ultrasonic Liquid Flow Transmitter Brochure, 6 pages (Apr. 2002).
Panametrics XMT868 Ultrapure Flow System Brochure, 4 pages (Apr. 2002).

(Continued)

*Primary Examiner*—Hezron Williams
*Assistant Examiner*—Jacques Saint Surin
(74) *Attorney, Agent, or Firm*—Fay Kaplun & Marcin, LLP

(57) ABSTRACT

An ultrasonic transducer for measuring a part with a coating having at least one acoustic transducer, and a buffer delay line having an impedance matched to an impedance of the coating.

6 Claims, 4 Drawing Sheets

10
12
12
14
18
$T_1$
$T_4$
$T_2$
$T_3$
H
16
22
20

OTHER PUBLICATIONS

Panametrics DF868 Ultrasonic Fixed Installation Liquid Flowmeter, 8 pages (Apr. 2002).

Panametrics PT878 Portable Liquid Flowmeter, 6 pages (Apr. 2002).

Panametrics Aquatrans Ultrasonic Flow Transmitter—Options and Specification, 4 pages (Apr. 2002).

Panametrics GC868 Brochure, 4 pages (Apr. 2002).

Scelzo, A Clamp-On Ultrasonic Flowmeter for Gases, Flow Control Magazine, 3 pages (2001).

Panametrics CEM68 for Continuous Emissions Monitoring Systems, 4 pages (Apr. 2002).

* cited by examiner

METHOD FOR MEASURING PART THICKNESS HAVING AN EXTERNAL COATING USING IMPEDANCE MATCHING DELAY LINES

BACKGROUND OF THE INVENTION

This invention relates to thickness measurement instruments, and in particular to ultrasound thickness measurement instruments.

In many applications it is helpful to know with accuracy the thickness of a part. A thickness measurement may be used to detect part wear and may indicate that a part should be replaced before the part mechanically fails. For example, thickness measurements are helpful in determining whether to replace pipes carrying fluids, e.g., liquids or gasses, before the pipe bursts or otherwise fails due to excessive wear. On the other hand, it is desirable to avoid replacing pipes that still have a considerable safe useful life. For this reason, the need for accuracy in the determination of the thickness of the part is paramount.

Ultrasound instruments have been used to measure the thickness of pipes and other parts. The time-of-flight (TOF) of an ultrasonic echo traveling through a part is used to determine the thickness of the part. The ultrasound velocity in the part is a known constant. Thus, the TOF provides an accurate indication of part thickness. Pulse-echo techniques are usually used for these ultrasound measurements. Instruments having dual transducers in a pitch-catch configuration may be utilized for ultrasonic thickness measurements.

Pipes and other parts often are coated with paint and other coatings that affect the propagation rate of ultrasound signals. The coating may corrode or become thin due to wear. Measurement of the thickness is needed to determine whether the coating needs to be repaired or reapplied, and whether the coated pipe should be replaced.

Ultrasound measurement of the thickness of coatings is problematic. Pulse echo ultrasound techniques rely on the time of flight (TOF) of echoes reflecting off internal features of the part. With a corroded coating, the echoes at the interface between the coating and underlying pipe often become distorted due to the corrosion. In some instances, the ultrasound instrument cannot detect an echo from the coating-pipe interface and cannot reliably measure the thickness of the coating. Accordingly, there is a long felt need for a system and method to measure the thickness of coatings on parts using ultrasound measurement techniques.

BRIEF DESCRIPTION OF THE INVENTION

The invention is a method to measure a thickness of a party with a coating using an ultrasonic transducer instrument having a buffer delay line and at least one transducer, the method comprising: selecting an impedance for the buffer delay line of a same order of magnitude as an impedance of a coating on the part; calibrating the instrument by determining a time of flight period ($T_{CAL2}$) from an acoustic pulse emission to an echo reception, wherein the echo reflects from an interface between the coating and underlying part; measuring a time of flight (TOF) from an acoustic pulse emission to an echo reception, wherein the echo reflects from a back surface of the underlying part; determining a thickness of the part based on a difference between the TOF and the $T_{CAL2}$.

DETAILED DESCRIPTION OF THE INVENTION

Figure 1:
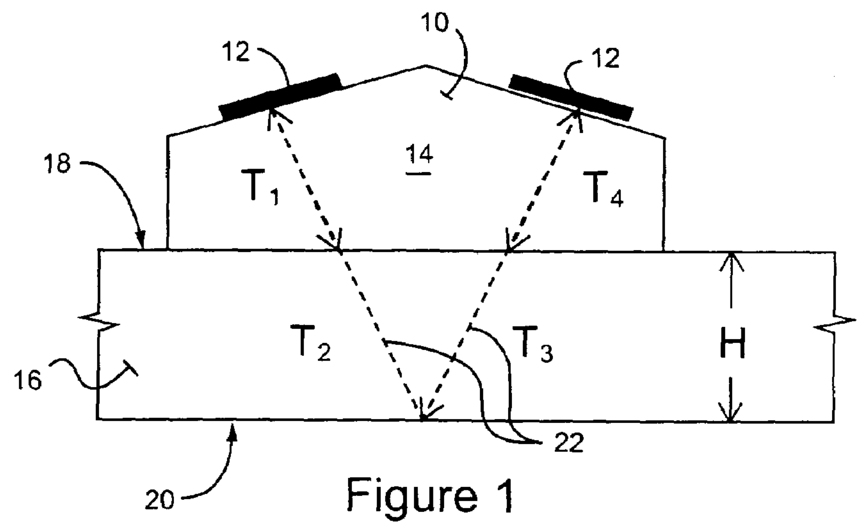
FIG. 1 is a schematic diagram of a dual transducer ultrasound instrument on an uncoated part.

FIG. 1 shows an ultrasound instrument 10 having dual transducers 12 mounted on a transducer buffer delay line 14. The transducers may be arranged in a pitch-catch orientation. The instrument is mounted on a part 16 so as to measure a thickness (H) of the part. The transducers emit ultrasound signals, e.g., acoustic pulses, that propagate through the delay line, pass into the part 16 and reflect off the front surface 18 and back surface 20 of the part. The propagation paths 22 of the ultrasound pulses from each of the transducers 12 indicate the outbound path of an acoustic pulse emitted from the transducer and the inward bound path of echoes reflected from the surfaces of the part. In a dual transducer instrument, each transducer 12 emits an ultrasound signal and receives the echoes reflected from the signals emitted from the other transducer. The buffer delay line 14 introduces a time delay in the signal propagation so that the transducers can switch from signal transmission to signal reception before the echoes return to the transducers. The dual transducers are mounted on the buffer delay line at a slight tilt angle such that signals transmitted from one transducer produce echoes that are received by the other transducer.

The time of flight (TOF) is the period from the transmission of an ultrasound pulse by one of the transducers 12 to when an echo of the pulse is received by the other transducer. The TOF may include periods during which the signal propagates through the delay line, e.g., $T_1$ and $T_4$, and periods during which the signal propagates through the part, e.g., $T_2$ and $T_3$.

FIG. 1 shows a part 16 that does not have coatings. Echoes are reflected from the front and back surfaces of the part, but not from coatings on the part—because there are no coatings in the part shown in FIG. 1. The dual transducer instrument 10 has a buffer delay line 14 separating the transducer crystal from the front surface 18 of the part 16. The TOF is given by the sum of the time delays associated with the different paths:

$$TOF=T_1+T_2+T_3+T_4 \quad \text{(Eq. 1)}$$

Where: $T_1$ is the time delay associated with the first leg (outbound) of signal propagation through the buffer 14; $T_2$ is the time delay associated with the first leg of signal propagation through the part; $T_3$ is the time delay associated with the second leg (echo inbound) of signal propagation in the part; and $T_4$ is the time delay associated with the second leg of signal propagation in the buffer. $T_1$ and $T_4$ can be measured during calibration ($T_{CAL}=T_1+T_4$) of the instrument 10 using each transducer in pulse echo mode. $T_{CAL}$ is indicative of the signal propagation time through the buffer delay line 14. The $T_{CAL}$ portion of the TOF is a constant applied during actual thickness measurements of the part.

The thickness (H) of the part 16 can be determined using equation (2) as follows:

$$H=V\text{part}*(\text{TOF}-T_{CAL})*k/2 \quad \text{(Eq. 2)}$$

Where: Vpart is the propagation velocity of the ultrasound signal through the part, and k is a geometrical correction factor accounting for the tilt angle between the two transducers 12 and the factor 2 of the pulse-echo.

Figure 2:
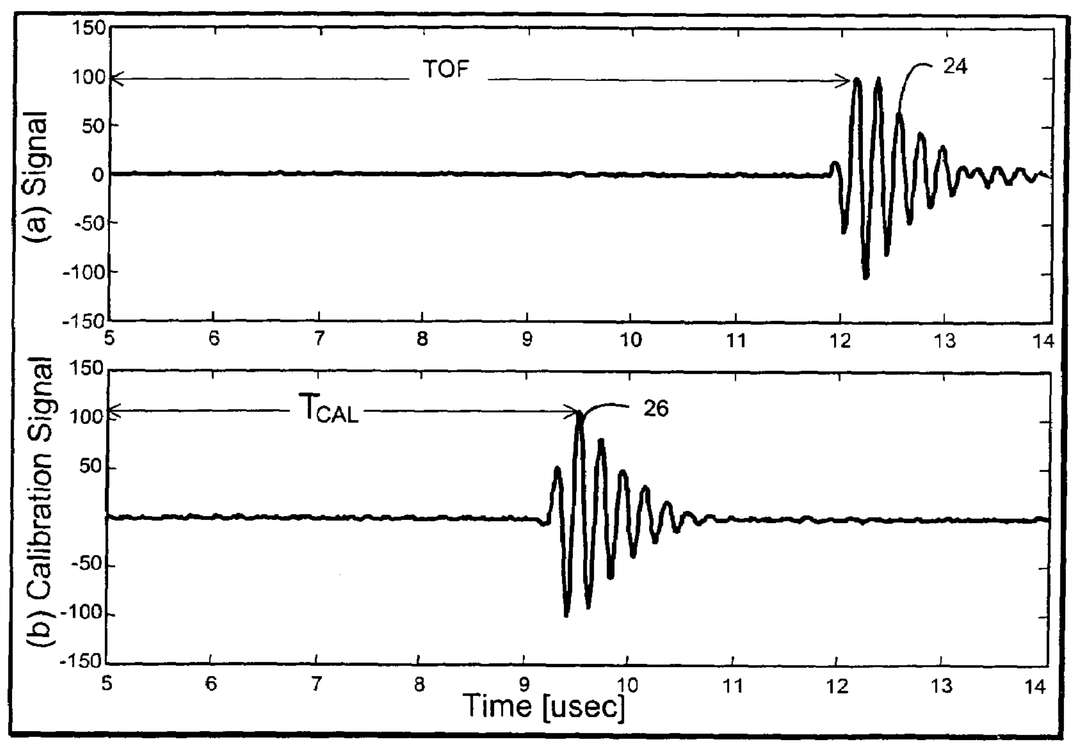
FIG. 2 are ultrasound signal time-of-flight graphs associates with the transducer and uncoated part show in FIG. 1.

FIG. 2 shows typical ultrasound echo signals acquired by the transducer for the measurement of the part 16 shown in FIG. 1. The graphs shown in FIG. 2 show the echo signal amplitude over a period of time. The first signal 24 represents the measurement a TOF (12.24 µsec) of an echo reflecting off of the back surface 20 of the part. The second signal 26 may be assigned as the calibration time ($T_{CAL}$=9.53 µsec) and indicates the period of the TOF during which the signals are passing through the buffer delay line 14. The second signal 26 was obtained by using the transducer in pulse-echo mode and measuring the signal reflected by the bottom surface of the delay line. Using Equation 2 and with Vpart=0.232 in/µsec, k=0.955, the thickness (H) is 0.300 inches for the part 16 shown in FIG. 1.

The part 16 in FIG. 1 does not have a surface coating. Many parts do have coatings of paint or other materials to protect the part or provide some beneficial property to the part. Measurement of the thickness of the coating or of a coated part is difficult because the coating has a different acoustic velocity and may introduce an error in ultrasonic measurement.

Figure 3:
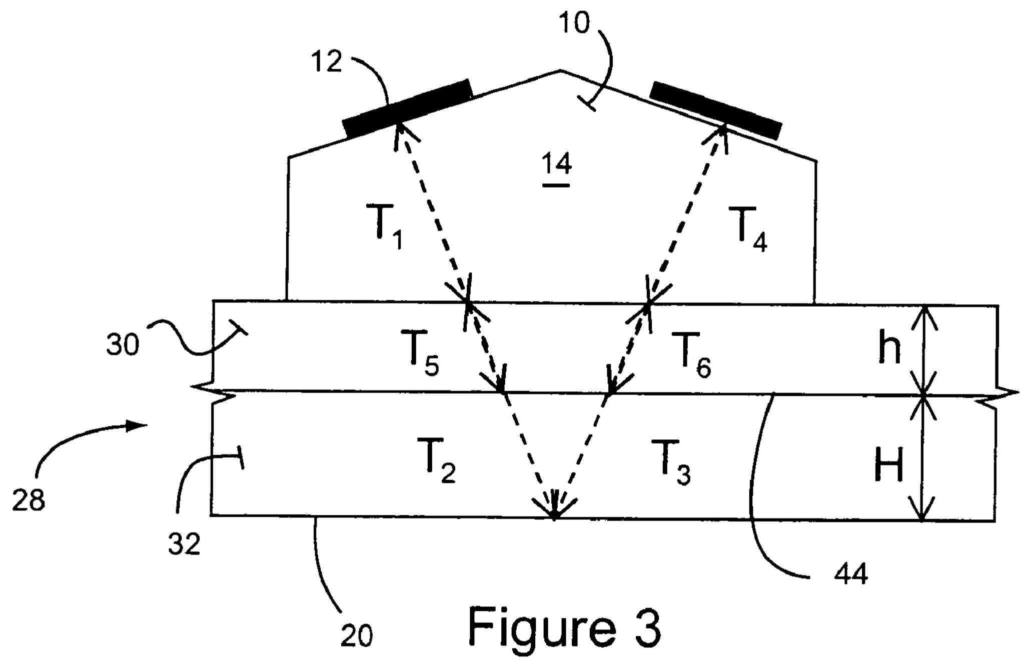
FIG. 3 is a schematic diagram of a dual transducer ultrasound instrument mounted on a coated part.

FIG. 3 shows a coated part 28 having a coating 30, e.g., paint, and an underlying part material 32. The TOF of an ultrasound signal propagating through the coating, part and buffer delay line as is indicated below in Equation 3:

$$\text{TOF}=T_1+T_2+T_3+T_4+T_5+T_6 \quad \text{(Eq. 3)}$$

Where: $T_5$ and $T_6$ are the time delays associated with the ultrasonic wave traveling through the coating, and $T_1$ to $T_4$ are the same as for the similarly referenced TOF periods shown in FIG. 1.

The time delays ($T_5$ and $T_6$) associated with the coatings can introduce an error in the measurement of the thickness of the part. The error (ET) in the measurement of the part thickness, e.g., the thickness (TC) of the coating or the thickness (H) of the part, can be determined using Equations 4a and 4b below:

$$ET=V\text{part}/V\text{coat}*(TC)*k \quad \text{(Eq. 4a)}$$

$$ET=V\text{part}/V\text{coat}*H*k \quad \text{(Eq. 4b)}$$

Where Vcoat is the propagation velocity of the ultrasound through the coating on the part. The ratio (Vpart/Vcoat) is usually a factor of two to three. In view of this rather high velocity ratio, the error (ET) introduced by the coating in the determination of the thickness of the coating or part can be quite high.

Figure 4:
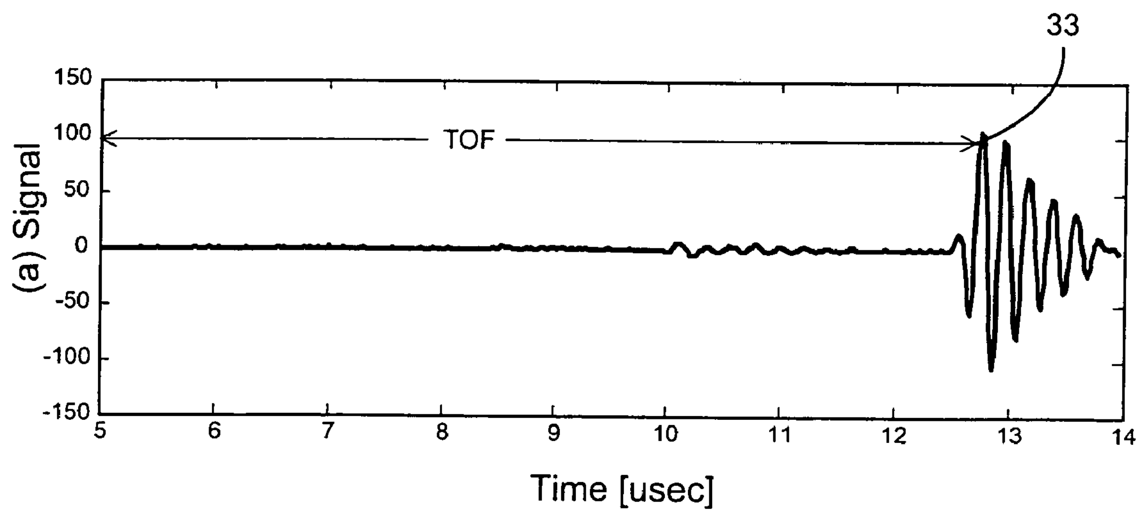
FIG. 4 is an TOF graph associated with the transducer and coated part shown in FIG. 3.

FIG. 4 is a chart showing the TOF of an ultrasound signal 33 associated with the coated part 28, where the coating is a paint layer having a thickness of 0.030 inches. The TOF is 12.84 µsec. Using equation 2, the estimated part thickness is 0.367 inches in contrast to the actual part thickness of 0.300. Accordingly, a measurement error (ET) of 0.067 inches has been introduced into the part thickness measurement due to the coating.

Figure 5:
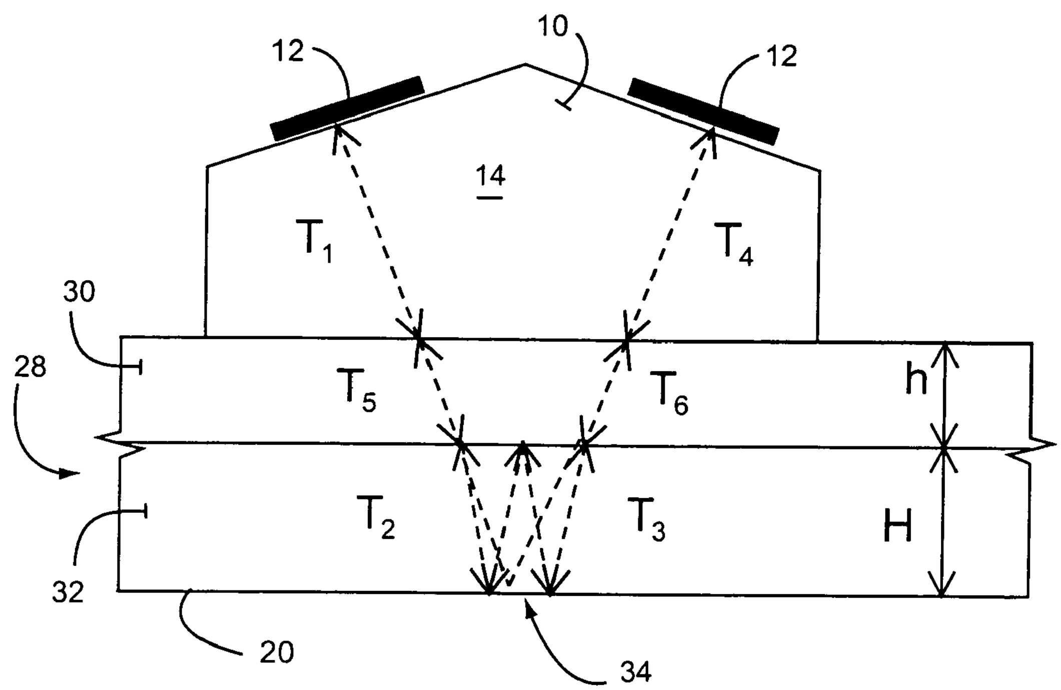
FIG. 5 is a schematic diagram of a dual transducer ultrasound instrument on a coated part and illustrating an echo-to-echo signal.

FIG. 5 is a schematic of a dual transducer ultrasound instrument 10 mounted on a coated part 28. The instrument senses echo-to-echo signals, as well as the transducer-to-echo signals. A echo-to-echo signal 34 is an ultrasound signal that includes two or more reflected echoes in the path of the signal. A portion of the echo that reflects off the back surface 20 will reflect off the front surface 18 and again off the back surface before propagating to the transducer.

Figure 6:
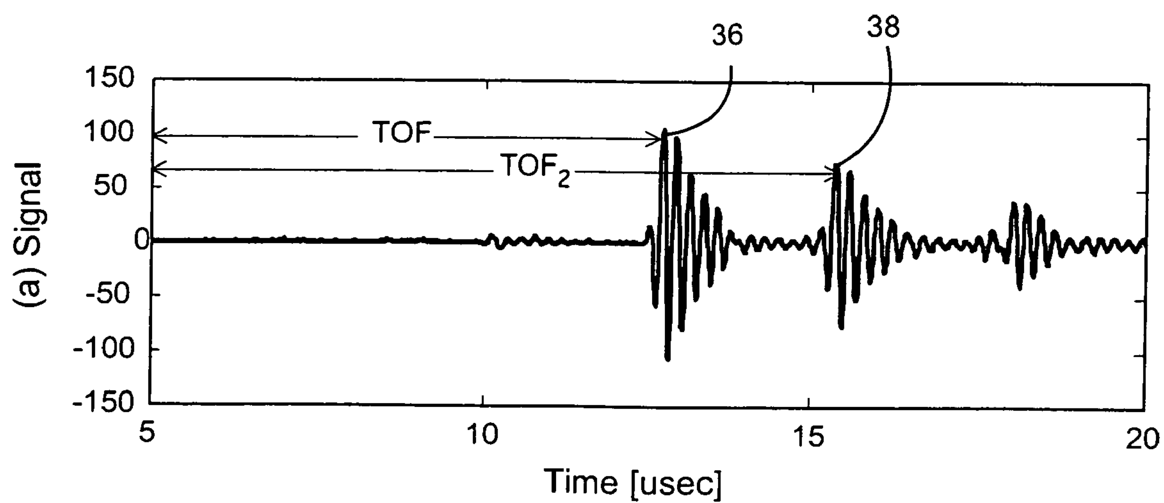
FIG. 6 is an TOF graph associated with the transducer and coated part shown in FIG. 5 and showing the $TOF_2$ of an echo-to-echo signal.

FIG. 6 is a chart showing the TOF of a sequence of echo signals. A first signal (TOF) 36 has a path ($T_1 \rightarrow T_5 \rightarrow T_2 \rightarrow T_3 \rightarrow T_6 \rightarrow T_4$) and does not include an echo-to-echo signal. A subsequent signal ($\text{TOF}_2$) 38 ($T_1 \rightarrow T_5 \rightarrow T_2 \rightarrow T_2 \rightarrow T_3 \rightarrow T_3 \rightarrow T_6 \rightarrow T_4$). Two successive echoes ($T_2 \rightarrow T_2 \rightarrow T_3 \rightarrow T_3$) of the same signal occur as can be used to determine the thickness of the part. The TOF of the first signal 36 is still given by equation 3. The $\text{TOF}_2$ for the second signal 38 is given by equation 5 below:

$$\text{TOF}_2=T_1+2T_2+2T_3+T_4+T_5+T_6 \quad \text{(Eq. 5)}$$

The thickness (H) of the part can be calculated using equation 6 below:

$$H=V\text{part}*(\text{TOF}_2-\text{TOF})*k/2 \quad \text{(Eq. 6)}$$

Using the prior example and the signals shown in FIG. 6 to read TOF, the $\text{TOF}_2$ is 15.55 µsec and TOF is 12.84 µsec. Applying equation 6, the thickness of the part H is measured as being 0.300 inches, which is accurate.

In principle, the echo-to-echo measurement is accurate. However in many corroded parts, the echo-to-echo signals are distorted and weak. In some cases these signals are almost null. Often, the echo-to-echo signals cannot be reliably used to determine $\text{TOF}_2$ and the echo-to-echo technique is not useful to measure the thickness of a part.

Another technique is needed to measure the thickness of a coating and the thickness of a coated part. Other prior art techniques utilize a magnetic measurement, such as Hall effect or Eddy current methods, to determine the thickness (h) of a coating. Once h is determined, then the part thickness (H) can be determined using equation 7 below:

$$H=V\text{part}*(\text{TOF}-T_{CAL})*k/2-V\text{part}/V\text{coating}*h*k \quad (7)$$

However, if there is any error in the determination of h and or of Vcoating by the Hall effect or Eddy current sensors, then the thickness of the part (H) cannot be accuracy determined. Another prior art technique is to determine $T_5$ and $T_6$ separately and then subtract them from the TOF measurement. Such a technique is shown in U.S. Pat. No. 6,035,717. These prior techniques for measuring the thickness of coated pipes have one or more problems, some of which are discussed above.

Another technique, which is the subject of this disclosure, is to impedance match the transducer buffer delay line buffer 14 in the ultrasound instrument 10 to the impedance of the coating 30 on a coated part 28. Pipes and other parts are typically coated with paint, epoxy or RTV-type material. These coatings have a typical acoustic impedance on the order of $3.0\times10^6$ Kg/m$^2$ sec. The delay line material in the buffer 14 of the transducer 12 may be selected such that it is impedance matched to the coating 30 on the part 28. By impedance matching the buffer delay line 14 to the coating, the reflection coefficient between the end of the delay line and the coating is extremely small ($R<0.1$). By impedance matching, the coating becomes an extension of the delay line for ultrasonic purposes. A plurality of buffer delay lines 14 may be available for selection and attachment to the transducer instrument 10, wherein each buffer delay line has a different impedance. In use, the buffer delay line having an impedance similar to that of the coating being measured.

Figure 7:
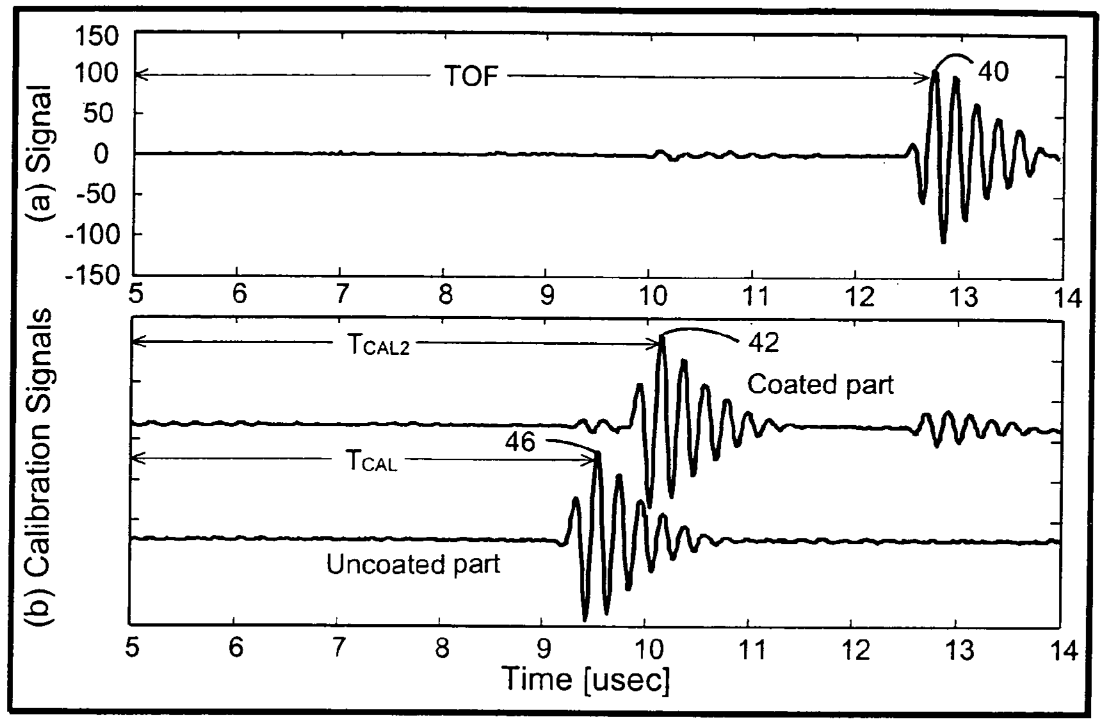
FIG. 7 is a pair of graphs showing a TOF of an ultrasound signal reflected from a back surface of a part, and a pair of calibration time of flight signals designated $T_{CAL}$ and $T_{CAL2}$.

FIG. 7 shows TOF graphs of a signal 40 that is of an echo reflected from the back surface 20 of a part; a calibration signal ($T_{CAL2}$) 42 that reflected off the interface 44 (FIG. 3) between the coating 30 and the underlying part 32, and the calibration signal ($T_{CAL}$) 46 performed on an uncoated part 16 (FIG. 1). The calibration of the instrument is performed while the transducer is mounted on the pipe. When the transducer is mounted on a coated part, the ultrasound signals pass through, without reflection, the interface 44 between the buffer delay line 14 and coating 30, because the buffer delay line is impedance matched to the coating. The calibration signal is relatively strong, at least as compared to echo-to-echo signals. The time of light of the calibration signal ($T_{CAL2}$) 42 is indicated by Equation 9 below with reference to FIG. 3:

$$T_{CAL2}=T_1+T_4+T_5+T_6 \quad \text{(Eq. 9)}$$

Using $T_{CAL2}$ the thickness (H) of underlying part 32 can be determined using Equation 10 below:

$$H=V\text{part}*(\text{TOF}-T_{CAL2})*k/2 \quad \text{(Eq. 10)}$$

Further, the thickness (h) of the coating is determined knowing $T_{CAL2}$ and the conventional calibration time of flight ($T_{CAL}$) 46 measured when the transducer is on an uncoated part. The coating thickness (h) may be determined using Equation 11 below:

$$h=V\text{coat}*(T_{CAL2}-T_{CAL})*k/2 \quad \text{(Eq. 11)}$$

The time of flight of the signals shown in FIG. 7 provide an example of the measurements of the part and coating thicknesses (H, h). The timing of the TOF 40 is 12.84 µsec, $T_{CAL}$ 46 is 9.53 µsec, and $T_{CAL2}$ 42 is 10.14 µsec. Applying equations 10 and 11, the part thickness (H) is determined to be 0.300 inches and the coating thickness (h) is determined to be 0.029 inches. Using impedance matching to determine a $T_{CAL2}$, the time of flight of signals passing through the buffer delay line and coating and reflecting from the coating-part interface 44 provides an accurate technique for measuring the thickness of a coating and the underlying part.

Figure 8:
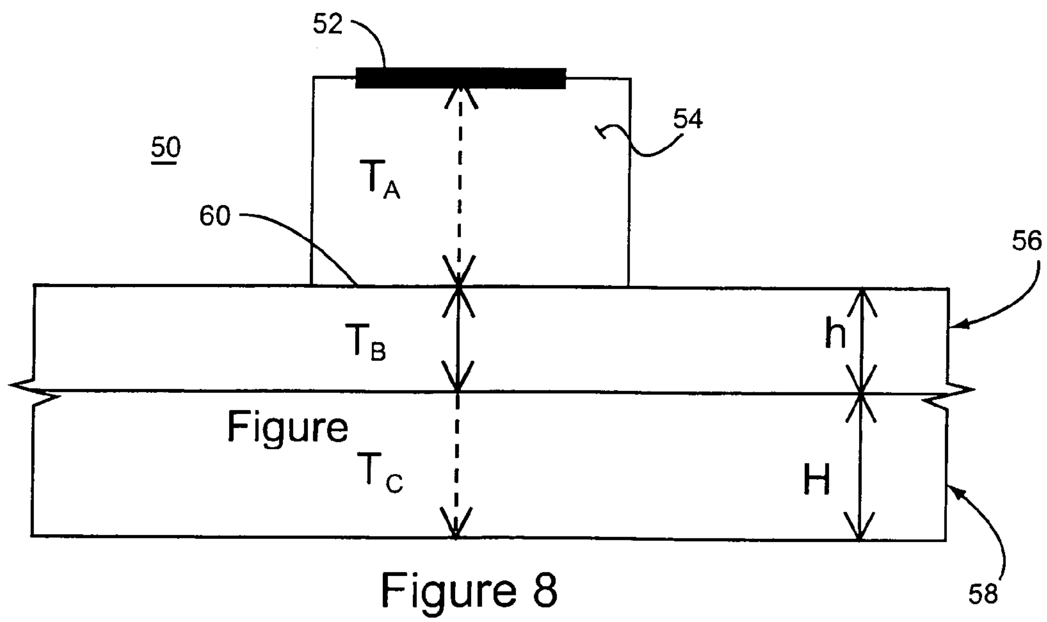
FIG. 8 is a schematic diagram of an ultrasound instrument having a single transducer and mounted on a coated part.

The technique of impedance matching the buffer delay line to the impedance of the coating may also be applied to an ultrasound instrument 50 having a single transducer 52, as is shown in FIG. 8. A instrument 50 having signal transducer 52 and a buffer delay line 54 is mounted on the coating 56 of a coated part 58. The propagation time through: the buffer delay line is represented by $T_A$, the coating is represented by $T_B$ an through the part is represented by $T_C$.

The traditional instrument calibration signal ($T_{CAL}$) indicates the acoustic propagation time through the buffer delay line, with the echo reflected from the bottom of the delay line 60. $T_{CAL}$ may be determined based on equation 12 below:

$$T_{CAL}=2*T_A \quad \text{(Eq. 12)}$$

The calibration signal ($T_{CAL2}$) indicates the acoustic propagation time through the buffer delay line ($T_A$) and coating ($T_B$). $T_{CAL2}$ may be determined based on equation 13 below:

$$T_{CAL2}=2*(T_A+T_B) \quad \text{(Eq. 13)}$$

The TOF of a signal reflecting from the back surface 20 of the part 58 may be determined based on equation 14 below:

$$\text{TOF}=2*(T_A+T_B+T_C) \quad \text{(Eq. 14)}$$

The part thickness (H) may be determined based on equation 15 below:

$$H=V\text{part}*(\text{TOF}-T_{CAL2})/2 \quad \text{(Eq. 15)}$$

The coating thickness (h) may be determined based on equation 16 below:

$$h=V\text{coat}*(T_{CAL2}-T_{CAL})/2 \quad \text{(Eq. 16)}$$

Please note that equations 15 and 16 are equivalent to equations 10 and 11, where k is taken as one.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method to measure a thickness of a part with a coating using an ultrasonic transducer instrument having a buffer delay line and at least one transducer, the method comprising:

a. selecting an impedance for the buffer delay line of a same order of magnitude as an impedance of a coating on the part;

b. calibrating the instrument by determining a time of flight period ($T_{CAL2}$) from an acoustic pulse emission to an echo reception, wherein the echo reflects from an interface between the coating and underlying part;

c. measuring a time of flight (TOF) from the acoustic pulse emission to a second echo reception, wherein the second echo reflects from a bottom surface of the underlying part; and d. determining a thickness of the part based on a difference between the TOF and the $T_{CAL2}$.

2. A method as in claim 1 wherein the determination of the thickness (H) of the part is made using the following equation:

$$H=V\text{part}*(\text{TOF}-T_{CAL2})*k/2$$

wherein Vpart is an acoustic velocity through the part and k is a geometrical correction factor accounting for an angle between a pair of transducers that are the at least one ultrasound transducer.

3. A method as in claim 1 wherein the determination of the thickness (H) of the part is made using the following equation:

$$H=V\text{part}*(\text{TOF}-T_{CAL2})/2$$

wherein Vpart is an acoustic velocity through the part and the at least one transducer is one transducer.

4. A method as in claim 1 further comprising:

e. calibrating the instrument by determining a time of flight period ($T_{CAL}$) from the acoustic pulse emission to a third echo reception, wherein the third echo reflects from a bottom surface of the buffer delay line, and f. determining a thickness of the coating based on a difference between the $T_{CAL}$ and the $T_{CAL2}$.

5. A method as in claim 4 wherein the determination of the thickness (h) of the coating is made using the following equation:

$$h=V\text{coat}*(T_{CAL2}-T_{CAL})*k/2$$

wherein Vcoat is an acoustic velocity through the coating and k is a geometrical correction factor accounting for an angle between a pair of transducers that are the at least one ultrasound transducer.

6. A method as in claim 4 wherein the determination of the thickness (h) of the coating is made using the following equation:

$$H=V\text{coat}*(T_{CAL2}-T_{CAL})/2$$

wherein Vcoat is an acoustic velocity through the coating and the at least one transducer is one transducer.

* * * * *